United States Patent
Cowley (10) Patent No.: US 10,881,424 B2
(45) Date of Patent: Jan. 5, 2021

(54) REMOVABLE FLUID RESERVOIR AND ULTRASONIC SURGICAL INSTRUMENT INCLUDING THE SAME

(71) Applicant: COVIDIEN LP, Mansfield, MA (US)

(72) Inventor: Matthew S. Cowley, Frederick, CO (US)

(73) Assignee: COVIDIEN LP, Mansfield, MA (US)

( * ) Notice: Subject to any disclaimer, the term of this patent is extended or adjusted under 35 U.S.C. 154(b) by 53 days.

(21) Appl. No.: 15/895,254

(22) Filed: Feb. 13, 2018

(65) Prior Publication Data

US 2019/0247073 A1    Aug. 15, 2019

(51) Int. Cl.
*A61B 17/32* (2006.01)
*A61B 17/00* (2006.01)

(52) U.S. Cl.
CPC ........... *A61B 17/320068* (2013.01); *A61B 17/320092* (2013.01); *A61B 2017/00398* (2013.01); *A61B 2017/00477* (2013.01); *A61B 2017/320074* (2017.08); *A61B 2017/320084* (2013.01); *A61B 2017/320094* (2017.08)

(58) Field of Classification Search
CPC ....... A61B 2017/320072; A61B 2017/320068; A61B 2017/32007; A61B 2017/320084; A61B 17/320758
See application file for complete search history.

(56) References Cited

U.S. PATENT DOCUMENTS

| 3,526,219 A * | 9/1970 | Lewis ............ A61B 17/320068 600/565 |
| 3,589,363 A | 6/1971 | Banko et al. |
| 3,805,787 A | 4/1974 | Banko |

(Continued)

FOREIGN PATENT DOCUMENTS

| JP | 10216140 | 9/1998 |
| JP | 2016154836 A | 9/2016 |

(Continued)

OTHER PUBLICATIONS

Extended European Search Report issued in European Application No. 19156615.7 dated Jun. 7, 2019, 7 pages.

(Continued)

*Primary Examiner* — Wade Miles
*Assistant Examiner* — Mohammed S Adam (57) ABSTRACT

A fluid reservoir includes a housing having a body, a leading end, and a trailing end enclosing a fluid chamber storing fluid therein, sealed inflow and outflow ports disposed at the leading end of the housing, and a heat exchanger disposed at the trailing end of the housing. An ultrasonic surgical instrument includes a housing defining a barrel portion and a fixed handle portion extending from the barrel portion, an ultrasonic transducer received at least partially within the barrel portion of the housing, a waveguide operably coupled to the ultrasonic transducer and extending distally from the housing to a blade configured to treat tissue with ultrasonic energy produced by the ultrasonic transducer and transmitted along the waveguide, and a fluid management system disposed within the housing. The fluid reservoir is configured for releasable engagement with the fixed handle portion to facilitate cooling of the blade with fluid.

20 Claims, 4 Drawing Sheets

(56) References Cited

U.S. PATENT DOCUMENTS

| | | | |
|---|---|---|---|
| 3,874,183 A * | 4/1975 | Tabet | B60K 11/00 |
| | | | 62/3.61 |
| 4,136,700 A | 1/1979 | Broadwin et al. | |
| 4,169,984 A | 10/1979 | Parisi | |
| 4,223,676 A | 9/1980 | Wuchinich et al. | |
| 4,476,867 A * | 10/1984 | Parks | A61M 1/3655 |
| | | | 165/253 |
| 4,516,398 A | 5/1985 | Wuchinich | |
| 4,526,571 A | 7/1985 | Wuchinich | |
| 4,587,958 A | 5/1986 | Noguchi et al. | |
| 4,660,573 A | 4/1987 | Brumbach | |
| 4,724,834 A | 2/1988 | Alperovich et al. | |
| 4,754,760 A | 7/1988 | Fukukita et al. | |
| 4,823,790 A | 4/1989 | Alperovich et al. | |
| 4,832,022 A | 5/1989 | Tjulkov et al. | |
| 4,832,683 A | 5/1989 | Idemoto et al. | |
| 4,835,746 A * | 5/1989 | Dessapt | C07F 11/00 |
| | | | 367/146 |
| 5,076,276 A | 12/1991 | Sakurai et al. | |
| 5,151,083 A | 9/1992 | Pichler | |
| 5,163,433 A * | 11/1992 | Kagawa | A61B 17/22012 |
| | | | 601/2 |
| 5,180,363 A | 1/1993 | Idemoto et al. | |
| 5,188,102 A | 2/1993 | Idemoto et al. | |
| 5,205,817 A | 4/1993 | Idemoto et al. | |
| 5,211,625 A | 5/1993 | Sakurai et al. | |
| 5,221,282 A | 6/1993 | Wuchinich | |
| 5,261,922 A | 11/1993 | Hood | |
| 5,318,570 A | 6/1994 | Hood et al. | |
| 5,358,505 A | 10/1994 | Wuchinich | |
| 5,391,144 A | 2/1995 | Sakurai et al. | |
| 5,397,293 A | 3/1995 | Alliger et al. | |
| 5,417,654 A | 5/1995 | Kelman | |
| 5,419,761 A | 5/1995 | Narayanan et al. | |
| 5,433,646 A * | 7/1995 | Tarng | F41B 9/0018 |
| | | | 446/473 |
| 5,462,522 A | 10/1995 | Sakurai et al. | |
| 5,484,398 A | 1/1996 | Stoddard | |
| 5,486,162 A | 1/1996 | Brumbach | |
| 5,531,597 A | 7/1996 | Foulkes et al. | |
| 5,560,362 A | 10/1996 | Sliwa, Jr. et al. | |
| 5,562,609 A | 10/1996 | Brumbach | |
| 5,582,588 A | 12/1996 | Sakurai et al. | |
| 5,624,393 A | 4/1997 | Diamond | |
| 5,702,360 A | 12/1997 | Dieras et al. | |
| 5,797,931 A | 8/1998 | Bito et al. | |
| 5,879,363 A | 3/1999 | Urich | |
| 5,906,628 A | 5/1999 | Miyawaki et al. | |
| 5,928,218 A | 7/1999 | Gelbfish | |
| 6,053,424 A | 4/2000 | Gipson et al. | |
| 6,073,492 A | 6/2000 | Rosselson et al. | |
| 6,379,371 B1 * | 4/2002 | Novak | A61B 17/320068 |
| | | | 606/169 |
| 6,380,264 B1 | 4/2002 | Jameson et al. | |
| 6,383,183 B1 | 5/2002 | Sekino et al. | |
| 6,443,969 B1 * | 9/2002 | Novak | A61B 17/320068 |
| | | | 606/169 |
| 6,454,781 B1 | 9/2002 | Witt et al. | |
| 6,551,337 B1 | 4/2003 | Rabiner et al. | |
| 6,770,071 B2 | 8/2004 | Woloszko et al. | |
| 6,869,439 B2 | 3/2005 | White et al. | |
| 6,953,461 B2 * | 10/2005 | McClurken | A61B 18/14 |
| | | | 606/51 |
| 7,533,830 B1 | 5/2009 | Rose | |
| 7,735,751 B2 | 6/2010 | Ehlert et al. | |
| 7,810,743 B2 * | 10/2010 | McNichols | A61K 9/0024 |
| | | | 239/102.2 |
| 7,869,307 B2 | 1/2011 | Yamada et al. | |
| 7,963,458 B2 | 6/2011 | McNichols et al. | |
| 8,025,672 B2 | 9/2011 | Novak et al. | |
| 8,048,095 B2 | 11/2011 | Babaev | |
| 8,109,925 B2 | 2/2012 | Voic et al. | |
| 8,191,732 B2 | 6/2012 | Ehlert et al. | |
| 8,236,019 B2 | 8/2012 | Houser | |
| 8,343,178 B2 | 1/2013 | Novak et al. | |
| 8,348,880 B2 | 1/2013 | Messerly et al. | |
| 8,628,534 B2 | 1/2014 | Jones et al. | |
| 8,641,609 B2 | 2/2014 | Hestad et al. | |
| 8,753,338 B2 * | 6/2014 | Widenhouse | A61B 18/1442 |
| | | | 606/41 |
| 8,974,478 B2 * | 3/2015 | Ross | A61B 17/3474 |
| | | | 606/169 |
| 8,986,303 B2 * | 3/2015 | Jimenez | A61B 18/12 |
| | | | 606/42 |
| 9,028,474 B2 * | 5/2015 | Brannan | A61B 17/3211 |
| | | | 606/33 |
| 9,044,261 B2 | 6/2015 | Houser | |
| 9,050,124 B2 | 6/2015 | Houser | |
| 9,113,930 B2 * | 8/2015 | Reid, Jr. | A61B 18/1477 |
| 9,113,943 B2 * | 8/2015 | Ross | A61B 17/320092 |
| 9,132,031 B2 | 9/2015 | Levinson | A61F 7/10 |
| 9,211,137 B2 | 12/2015 | Voic | |
| 9,239,036 B2 | 1/2016 | Ehlert et al. | |
| 9,271,751 B2 | 3/2016 | Houser et al. | |
| 9,276,300 B2 | 3/2016 | Mueller | |
| 9,320,528 B2 | 4/2016 | Voic et al. | |
| 9,387,005 B2 * | 7/2016 | Voic | A61B 17/14 |
| 9,554,809 B2 * | 1/2017 | Lark | A61B 17/1613 |
| 9,622,767 B2 * | 4/2017 | Stoddard | A61B 17/320092 |
| 9,764,166 B2 * | 9/2017 | Stoddard | A61B 17/320092 |
| 9,848,899 B2 * | 12/2017 | Sliwa | A61B 18/18 |
| 10,004,529 B2 * | 6/2018 | Stokes | A61B 17/320092 |
| 10,206,705 B2 * | 2/2019 | Estera | A61B 17/26 |
| 10,206,735 B2 * | 2/2019 | Kaveckis | A61B 18/1492 |
| 10,342,566 B2 * | 7/2019 | Stoddard | A61B 17/320016 |
| 10,357,271 B2 * | 7/2019 | Gitman | A61B 90/35 |
| 2001/0025179 A1 | 9/2001 | Levine | |
| 2001/0039419 A1 | 11/2001 | Francischelli et al. | |
| 2002/0087157 A1 | 7/2002 | Sliwa et al. | |
| 2002/0183774 A1 | 12/2002 | Witt et al. | |
| 2003/0040672 A1 * | 2/2003 | Ogura | A61B 17/320068 |
| | | | 600/437 |
| 2003/0163131 A1 | 8/2003 | Manna et al. | |
| 2003/0204199 A1 | 10/2003 | Novak et al. | |
| 2004/0010246 A1 | 1/2004 | Takahashi | |
| 2004/0073209 A1 | 4/2004 | Manna et al. | |
| 2004/0087972 A1 | 5/2004 | Mulholland et al. | |
| 2004/0102770 A1 * | 5/2004 | Goble | A61B 17/3423 |
| | | | 606/34 |
| 2004/0204728 A1 | 10/2004 | Haefner | |
| 2004/0234924 A1 | 11/2004 | Hickok et al. | |
| 2004/0241608 A1 | 12/2004 | Hickok | |
| 2005/0060012 A1 * | 3/2005 | Voorhees | A61F 7/02 |
| | | | 607/96 |
| 2006/0195106 A1 | 8/2006 | Jones et al. | |
| 2006/0211943 A1 | 9/2006 | Beaupre | |
| 2006/0264929 A1 * | 11/2006 | Goble | A61B 18/1402 |
| | | | 606/48 |
| 2006/0265035 A1 * | 11/2006 | Yachi | A61B 17/320092 |
| | | | 607/101 |
| 2007/0021765 A1 | 1/2007 | Sakai | |
| 2007/0088217 A1 | 4/2007 | Babaev | |
| 2007/0162050 A1 | 7/2007 | Sartor | |
| 2008/0058845 A1 | 3/2008 | Shimizu et al. | |
| 2008/0234709 A1 | 9/2008 | Houser | |
| 2008/0281200 A1 | 11/2008 | Voic et al. | |
| 2009/0030437 A1 | 1/2009 | Houser et al. | |
| 2009/0036914 A1 * | 2/2009 | Houser | A61B 17/29 |
| | | | 606/169 |
| 2009/0118751 A1 | 5/2009 | Wiener et al. | |
| 2009/0149930 A1 * | 6/2009 | Schenck | A61B 18/14 |
| | | | 607/100 |
| 2009/0155091 A1 * | 6/2009 | Ehlert | F04B 15/02 |
| | | | 417/53 |
| 2009/0270899 A1 | 10/2009 | Carusillo et al. | |
| 2009/0306550 A1 | 12/2009 | Babaev | |
| 2009/0306694 A1 | 12/2009 | Babaev | |
| 2009/0314748 A1 | 12/2009 | Rao et al. | |
| 2009/0318944 A1 | 12/2009 | Kimura et al. | |
| 2010/0106173 A1 | 4/2010 | Yoshimine | |
| 2010/0274236 A1 | 10/2010 | Krimsky | |
| 2012/0059289 A1 | 3/2012 | Nield et al. | |

(56) References Cited

U.S. PATENT DOCUMENTS

| | | | |
|---|---|---|---|
| 2012/0253371 A1 | 10/2012 | Ross et al. | |
| 2013/0072950 A1* | 3/2013 | Ross | A61B 17/3474 606/169 |
| 2013/0085554 A1* | 4/2013 | Belson | A61F 7/0085 607/105 |
| 2013/0090576 A1* | 4/2013 | Stulen | A61B 17/320092 601/2 |
| 2013/0172876 A1* | 7/2013 | Heard | A61B 18/148 606/41 |
| 2013/0184729 A1* | 7/2013 | Yasunaga | A61B 17/320092 606/169 |
| 2014/0005668 A1* | 1/2014 | Rhee | A61B 34/30 606/45 |
| 2014/0114335 A1 | 4/2014 | Banko | |
| 2014/0135804 A1 | 5/2014 | Weisenburgh, II et al. | |
| 2014/0207066 A1* | 7/2014 | Yavorsky | A61M 5/1413 604/151 |
| 2014/0276849 A1 | 9/2014 | Voic | |
| 2014/0336686 A1 | 11/2014 | Houser et al. | |
| 2015/0057692 A1 | 2/2015 | Voic | |
| 2015/0073457 A1* | 3/2015 | Stoddard | A61B 17/320092 606/169 |
| 2015/0073458 A1* | 3/2015 | Stoddard | A61B 17/320068 606/169 |
| 2015/0088137 A1 | 3/2015 | Manna | |
| 2015/0148832 A1 | 5/2015 | Boudreaux et al. | |
| 2015/0148833 A1 | 5/2015 | Stokes et al. | |
| 2015/0148834 A1 | 5/2015 | Gee et al. | |
| 2015/0148835 A1 | 5/2015 | Faller et al. | |
| 2015/0157356 A1* | 6/2015 | Gee | A61B 18/1445 606/169 |
| 2015/0164535 A1 | 6/2015 | Felder et al. | |
| 2015/0164536 A1 | 6/2015 | Czarnecki et al. | |
| 2015/0164537 A1 | 6/2015 | Cagle et al. | |
| 2015/0164538 A1 | 6/2015 | Aldridge et al. | |
| 2015/0165240 A1* | 6/2015 | Stoddard | A61B 17/320092 606/171 |
| 2015/0173791 A1 | 6/2015 | Ross et al. | |
| 2015/0182232 A1 | 7/2015 | Peterson et al. | |
| 2015/0182251 A1 | 7/2015 | Messerly et al. | |
| 2015/0196318 A1 | 7/2015 | Messerly et al. | |
| 2015/0257780 A1 | 9/2015 | Houser | |
| 2015/0257781 A1 | 9/2015 | Houser et al. | |
| 2015/0282878 A1* | 10/2015 | Kindermann | A61B 18/18 606/9 |
| 2015/0297255 A1 | 10/2015 | Fan et al. | |
| 2015/0327883 A1 | 11/2015 | Messerly et al. | |
| 2015/0328484 A1 | 11/2015 | Messerly et al. | |
| 2015/0351841 A1 | 12/2015 | Whiteside et al. | |
| 2016/0082292 A1* | 3/2016 | Kudo | A61B 17/320092 601/2 |
| 2016/0089155 A1 | 3/2016 | Lark et al. | |
| 2016/0129285 A1 | 5/2016 | Mikus et al. | |
| 2016/0143657 A1* | 5/2016 | Estera | A61B 17/26 606/110 |
| 2016/0143658 A1* | 5/2016 | Stokes | A61B 17/320092 606/169 |
| 2016/0143659 A1* | 5/2016 | Glutz | A61B 17/320092 606/171 |
| 2016/0144204 A1 | 5/2016 | Akagane | |
| 2016/0157885 A1 | 6/2016 | Lauchner | |
| 2016/0195450 A1 | 7/2016 | Akagane | |
| 2017/0281215 A1* | 10/2017 | Stoddard | A61B 17/320016 |
| 2017/0281216 A1* | 10/2017 | Stoddard | A61B 17/320016 |
| 2017/0325837 A1* | 11/2017 | Thompson | A61B 17/320092 |
| 2018/0224238 A1* | 8/2018 | Smith | F41B 9/0006 |

FOREIGN PATENT DOCUMENTS

| | | |
|---|---|---|
| JP | 2017538566 A | 12/2017 |
| WO | 2011006009 A1 | 1/2011 |

OTHER PUBLICATIONS

Japanese Office Action issued in corresponding Appl. No. JP 2019-023400 dated Dec. 24, 2019, together with English language translation (9 pages).

\* cited by examiner

REMOVABLE FLUID RESERVOIR AND ULTRASONIC SURGICAL INSTRUMENT INCLUDING THE SAME

BACKGROUND

Technical Field

The present disclosure relates to surgical instruments and, in particular, to a removable fluid reservoir and ultrasonic surgical instrument including the same to facilitate cooling of the surgical instrument.

Background of Related Art

Energy-based tissue treatment is well known in the art. Various types of energy (e.g., electrical, ultrasonic, microwave, cryogenic, thermal, laser, etc.) are applied to tissue to achieve a desired result. Ultrasonic energy, for example, may be delivered to tissue to treat, e.g., coagulate and/or cut, tissue.

Ultrasonic surgical instruments, for example, typically include a waveguide having a transducer coupled thereto at a proximal end of the waveguide and an end effector disposed at a distal end of the waveguide. The waveguide transmits ultrasonic energy produced by the transducer to the end effector for treating tissue at the end effector. The end effector may include a blade, hook, ball, shears, etc., and/or other features such as one or more jaws for grasping or manipulating tissue. During use, the waveguide and/or end effector of an ultrasonic surgical instrument can reach temperatures greater than 200° C.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

Provided in accordance with aspects of the present disclosure is a fluid reservoir configured for releasable engagement with an ultrasonic surgical instrument. The fluid reservoir includes a housing including a body, a leading end, and a trailing end enclosing a fluid chamber configured for storing fluid therein. The fluid reservoir further includes sealed inflow and outflow ports disposed at the leading end of the housing and a heat exchanger disposed at the trailing end of the housing.

In an aspect of the present disclosure, the fluid reservoir further includes inflow and outflow shafts operably coupled to the sealed inflow and outflow ports, respectively, and extending into the fluid chamber.

In another aspect of the present disclosure, the inflow and outflow shafts define different lengths such that open ends of the inflow and outflow shafts are spaced-apart from one another along a length of the fluid chamber.

In still another aspect of the present disclosure, the heat exchanger includes a plurality of fins configured to facilitate heat exchange between an exterior and an interior of the housing.

In yet another aspect of the present disclosure, the body defines a guide slot along a substantial portion of a length thereof that is configured to facilitate aligned insertion of the housing into an ultrasonic surgical instrument.

In still yet another aspect of the present disclosure, the sealed inflow and outflow ports are each configured to be punctured by a needle.

An ultrasonic surgical instrument provided in accordance with aspects of the present disclosure includes a housing defining a barrel portion and a fixed handle portion extending from the barrel portion. The fixed handle portion defines an internal cavity. The ultrasonic surgical instrument further includes an ultrasonic transducer received at least partially within the barrel portion of the housing, a waveguide operably coupled to the ultrasonic transducer and extending distally from the housing to a blade configured to treat tissue with ultrasonic energy produced by the ultrasonic transducer and transmitted along the waveguide, a fluid management system disposed within the housing, and a fluid reservoir releasably engageable within the internal cavity of the fixed handle portion of the housing. The fluid reservoir includes a body, a leading end, and a trailing end enclosing a fluid chamber storing fluid therein. The fluid reservoir further includes inflow and outflow ports disposed at the leading end and a heat exchanger disposed at the trailing end. Upon engagement of the fluid reservoir within the internal cavity, the inflow and outflow ports are operably coupled with the fluid management system to enable fluid from the fluid reservoir to be circulated to cool the blade.

In an aspect of the present disclosure, the inflow and outflow ports of the fluid reservoir are sealed and the fluid management system includes inflow and outflow needles configured to puncture the sealed inflow and outflow ports, respectively, to fluidly couple the fluid management system with the fluid reservoir.

In another aspect of the present disclosure, the fluid reservoir further includes inflow and outflow shafts operably coupled to the inflow and outflow ports, respectively, and extending into the fluid chamber. The inflow and outflow shafts may define different lengths such that open ends of the inflow and outflow shafts are spaced-apart from one another along a length of the fluid chamber.

In still another aspect of the present disclosure, the heat exchanger includes a plurality of fins configured to facilitate heat exchange between an exterior and an interior of the fluid reservoir. The heat exchanger may remain external of the housing when the fluid reservoir is engaged within the internal cavity.

In yet another aspect of the present disclosure, the fixed handle portion includes a guide rail disposed within the internal cavity and the body of the fluid reservoir defines a guide slot configured to receive the guide rail to guide insertion of the fluid reservoir into the internal cavity.

In still yet another aspect of the present disclosure, the fluid management system includes an inflow conduit communicating with a lumen disposed within the waveguide for circulating fluid from the fluid reservoir through the waveguide.

In another aspect of the present disclosure, the fluid management system includes a fluid pump configured to pump fluid at least one of to or from the fluid reservoir.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1:
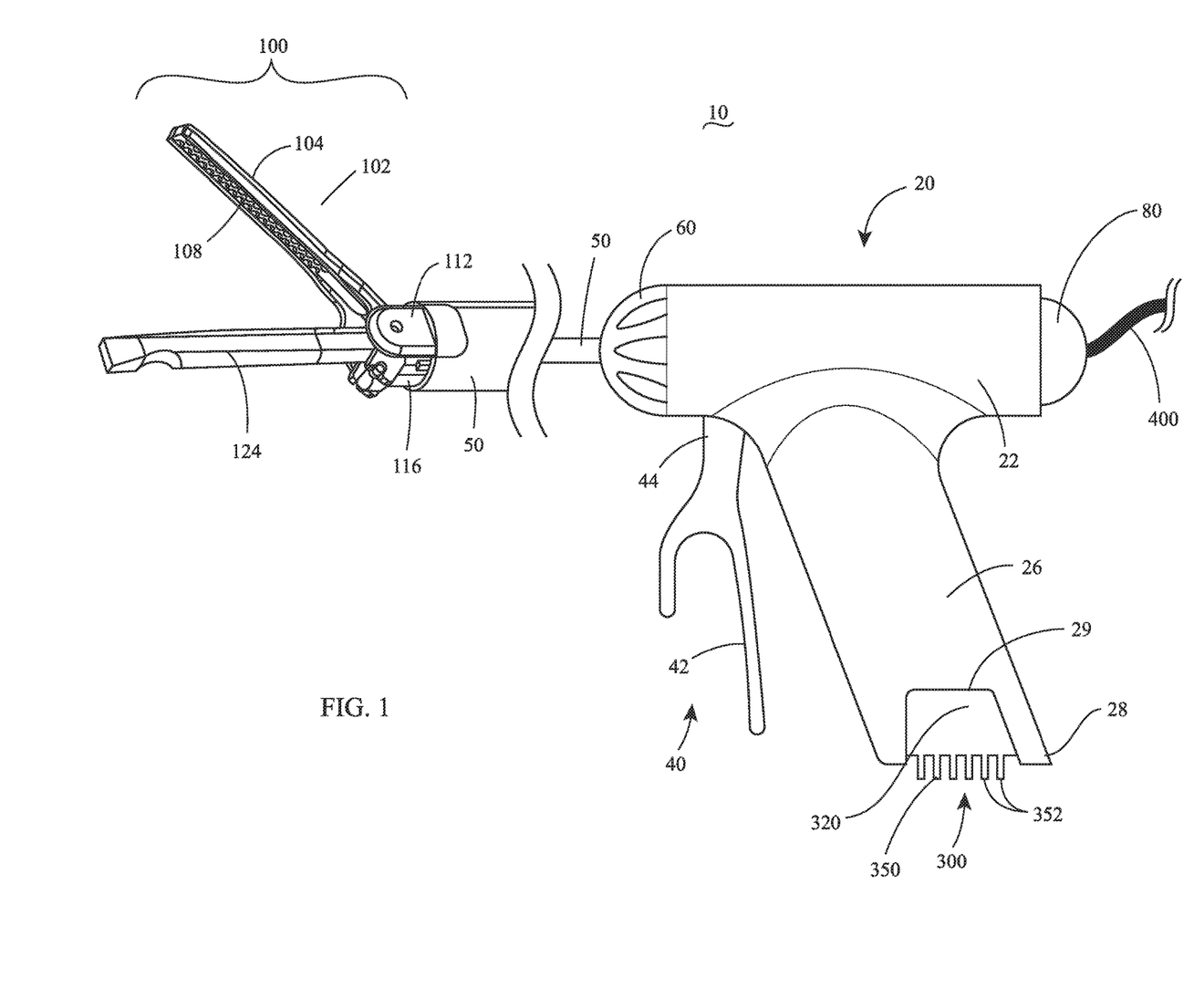
FIG. 1 is a perspective view of an ultrasonic surgical instrument provided in accordance with the present disclosure, wherein the distal end thereof is enlarged to better illustrate the components and features thereof.
Figure 2:
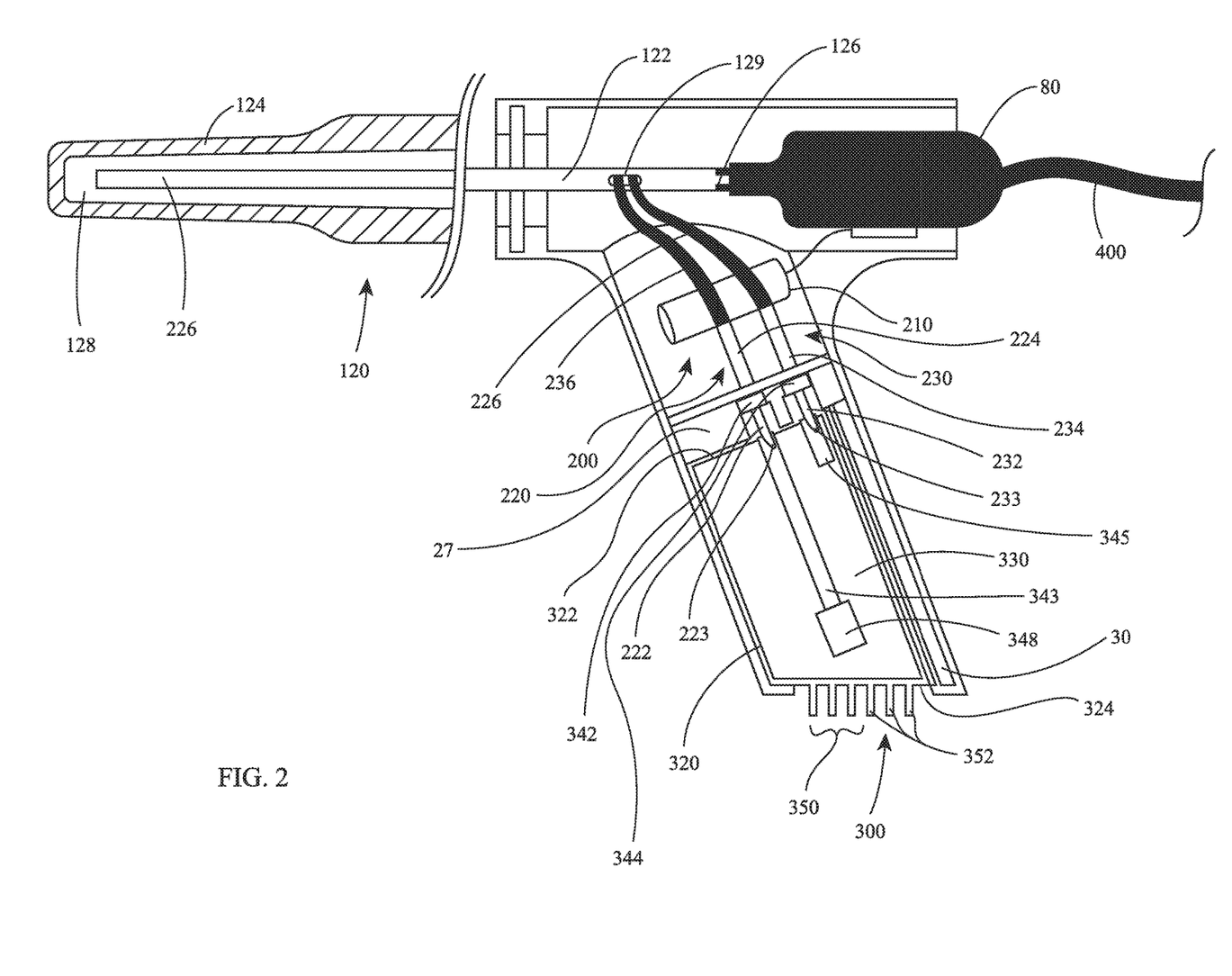
FIG. 2 is a side view of the ultrasonic surgical instrument of FIG. 1 with components removed, wherein the distal end thereof is enlarged and shown in cross-section to better illustrate features thereof.

Referring to FIGS. 1 and 2, an ultrasonic surgical instrument provided in accordance with the aspects and features of the present disclosure is shown generally identified by reference numeral 10. Ultrasonic surgical instrument 10 includes a housing 20, a movable handle 40 operably coupled to housing 20, a shaft 50 extending distally from housing 20, a rotation knob 60 supported on housing 20 and configured for rotating shaft 50 relative to housing 20, and an ultrasonic transducer 80 removably engageable with housing 20. Ultrasonic surgical instrument 10 further includes an end effector assembly 100 disposed at a distal end of shaft 50, a waveguide 120 extending through housing 20 and shaft 50 and operably coupling ultrasonic transducer 80 to end effector assembly 100, a drive assembly (not shown) operably coupled between movable handle 40 and end effector assembly 100, and an activation assembly (not shown) operably coupled to housing 20 or remotely disposed relative to housing 20 for enabling the selective supply of energy to ultrasonic transducer 80 to drive ultrasonic transducer 80. Ultrasonic surgical instrument 10 additionally includes a fluid management assembly 200 disposed within housing 20, a fluid reservoir 300 configured for releasable engagement with housing 20 and fluid management assembly 200, and a cable 400 configured to connect to a generator (not shown) or other power source for driving ultrasonic transducer 80.

Housing 20 defines a longitudinally-extending barrel portion 22 and a fixed handle portion 26 extending obliquely from barrel portion 22 to define a pistol-grip style configuration of housing 20. Barrel portion 22 of housing 20 is configured to removably receive at least a portion of ultrasonic transducer 80 therein to enable ultrasonic transducer 80 to operably couple with waveguide 120. Barrel portion 22 further defines a distal opening through which shaft 50, the drive sleeve of the drive assembly (not shown), and waveguide 120 extend in substantially coaxial arrangement.

Fixed handle portion 26 of housing 20 is positioned adjacent movable handle 40 to enable a user to grasp fixed handle portion 26 of housing 20 and manipulate movable handle 40 with a single hand. Fixed handle portion 26, more specifically, defines an interior cavity 27 having an open lower end 28 to enable receipt of fluid reservoir 300 therein, as detailed below. Fixed handle portion 26 further defines a pair of opposed cut-outs 29 adjacent open lower end 28 thereof, on opposing sides of fixed handle portion 26. Fixed handle portion 26 also includes a guide rail 30 disposed on an interior surface of fixed handle portion 26 and extending into interior cavity 27. Guide rail 30 extends a substantial portion of the length of fixed handle portion 26, e.g., at least 50% of the length of fixed handle portion 26 or, in embodiments, at least 75% of the length of fixed handle portion 26.

Movable handle 40 includes a grasping portion 42 configured to facilitate grasping and manipulation by a user. Movable handle 40 further includes a flange portion 44 extending into barrel portion 22 of housing 20. Flange portion 44 is pivotably coupled to housing 20 within housing 20 and is operably coupled to the drive assembly (not shown) of ultrasonic surgical instrument 10 such that pivoting of movable handle 40 relative to fixed handle portion 26 of housing 20 from a spaced-apart position towards an approximated position pivots clamp arm 102 of end effector assembly 100 relative to blade 124 of end effector assembly 100 from an open position to a clamping position for clamping tissue therebetween.

With continued reference to FIGS. 1 and 2, shaft 50 is rotatably supported by housing 20 and extends distally through a distal opening of barrel portion 22 of housing 20. Shaft 50 includes end effector assembly 100 disposed at a distal end thereof. Shaft 50 is disposed about the drive sleeve of the drive assembly (not shown), although it is also contemplated that this configuration be reversed, e.g., wherein the drive sleeve is disposed about shaft 50. Shaft 50 is longitudinally fixed relative to housing 20 but is rotatable relative thereto in response to rotation of rotation knob 60 relative to housing 20 via coupling therebetween. Rotation knob 60 is also coupled to the drive sleeve and waveguide 120 such that rotation of rotation knob 60 likewise rotates the drive sleeve, waveguide 120, and ultrasonic transducer 80 relative to housing 20 in response to rotation of rotation knob 60 relative to housing 20.

End effector assembly 100 includes clamp arm 102, blade 124 of waveguide 120, a pair of clevis members 112 (only one clevis member 112 is illustrated in FIG. 1 with the other being obstructed), and a drive link 116. Clamp arm 102 includes a frame 104 and a tissue pad 108 engaged with frame 104. Frame 104 of clamp arm 102 is pivotably coupled to a distal end portion of shaft 50 by way of clevis members 112. Drive link 116 is coupled between frame 104 of clamp arm 102 and a distal end portion of the drive sleeve such that translation of the drive sleeve translates drive link 116 to thereby pivot clamp arm 102 between the open and clamping positions.

Waveguide 120 defines a body 122, a blade 124 extending from the distal end of body 122, and a proximal connector 126 extending from the proximal end of body 122. Waveguide 120 defines an internal lumen 128 extending from a proximal portion thereof into blade 124. Internal lumen 128 is disposed in communication with a proximal port 129 defined through body 122 of waveguide 120 towards the proximal end thereof to enable the inflow and outflow of fluid into and out of internal lumen 128, as detailed below. In embodiments, a rotary manifold (not shown) is provided to enable the inflow and outflow of fluid into and out of internal lumen 128 while allowing waveguide 120 to rotate through 360 degrees relative to housing 20.

Internal lumen 128 of waveguide 120 defines a closed distal end within blade 124. Blade 124, as noted above, forms part of end effector assembly 100 in that blade 124 is positioned to oppose clamp arm 102 such that pivoting of clamp arm 102 from the open position to the clamping position enables clamping of tissue between clamp arm 102 and blade 124. Blade 124 may define a linear configuration as shown, or may define a curved configuration.

Proximal connector 126 of waveguide 120 is configured to enable engagement of waveguide 120 with ultrasonic transducer 80, e.g., via a threaded engagement or other suitable engagement, such that mechanical motion produced by ultrasonic transducer 80 is capable of being transmitted along waveguide 120 to blade 124 for treating tissue clamped between blade 124 and clamp arm 102 or positioned adjacent blade 124.

The drive assembly (not shown) operably couples movable handle 40 with clamp arm 102 such that actuation of movable handle 40 pivots clamp arm 102 between the open and clamping positions. The activation assembly (not shown) may include a button or other suitable actuator enabling enable manual manipulation by a user. In some embodiments, the activation assembly includes a two-mode button wherein actuation to a first actuated position supplies energy to ultrasonic transducer 80 corresponding to a "LOW" power mode, and wherein actuation to a second actuated position supplies energy to ultrasonic transducer 80 corresponding to a "HIGH" power mode.

Continuing with reference to FIGS. 1 and 2, fluid management assembly 200 is disposed within housing 20 and includes a fluid pump 210, an inflow fluid assembly 220, and an outflow fluid assembly 230. Inflow fluid assembly 220 includes a hollow needle 222 extending into interior cavity 27 of fixed handle portion 26 of housing 20 and defining a sharp tip 223 therein, a first conduit segment 224 configured to couple hollow needle 222 with fluid pump 210, and a second conduit segment 226 extending from fluid pump 210 through proximal port 129 of waveguide 120 and distally through internal lumen 128 of waveguide 120 to a position adjacent but distally-spaced from the closed distal end of internal lumen 128. Outflow fluid assembly 230 includes a hollow needle 232 extending into interior cavity 27 of fixed handle portion 26 of housing 20 and defining a sharp tip 233 therein, a first conduit segment 234 configured to couple hollow needle 232 with fluid pump 210, and a second conduit segment 236 extending from fluid pump 210 into proximal port 129 of waveguide 120. Unlike second conduit segment 226 of inflow fluid assembly 220, second conduit segment 236 of outflow fluid assembly 230 does not extend distally through waveguide 120 into blade 124. Rather, second conduit segment 236 terminates within internal lumen 128 adjacent to proximal port 129 of waveguide or extends partially through internal lumen 128 of waveguide 120 without extending into blade 124. However, other configurations of the inflow and outflow paths through waveguide 120 are also contemplated.

Fluid pump 210 may be a piezoelectric microfluidic pump or other microfluidic pumps such as micro-peristaltic pumps, syringe pumps, etc. and may be connected to the generator (or other power source) through cable 400 for powering fluid pump 210 or may include a battery that powers fluid pump 210. Fluid pump 210 is configured to draw fluid into hollow needle 222 and first conduit segment 224 and pump the fluid through second conduit segment 226 into internal lumen 128 within blade 124 of waveguide 120. Additionally or alternatively, fluid pump 210 is configured to draw fluid proximally from blade 124 within the annular space defined between second conduit segment 226 of inflow fluid assembly 220 and the interior wall of waveguide 120 that defines internal lumen 128, into second conduit segment 236 of outflow fluid assembly 230 and to pump the fluid through first conduit segment 234 and needle 232 of outflow fluid assembly 230. In either configuration, fluid management assembly 200 enables the circulation of fluid through waveguide 120 and, specifically, blade 124 of waveguide 120, to facilitate cooling of blade 124.

Figure 3:
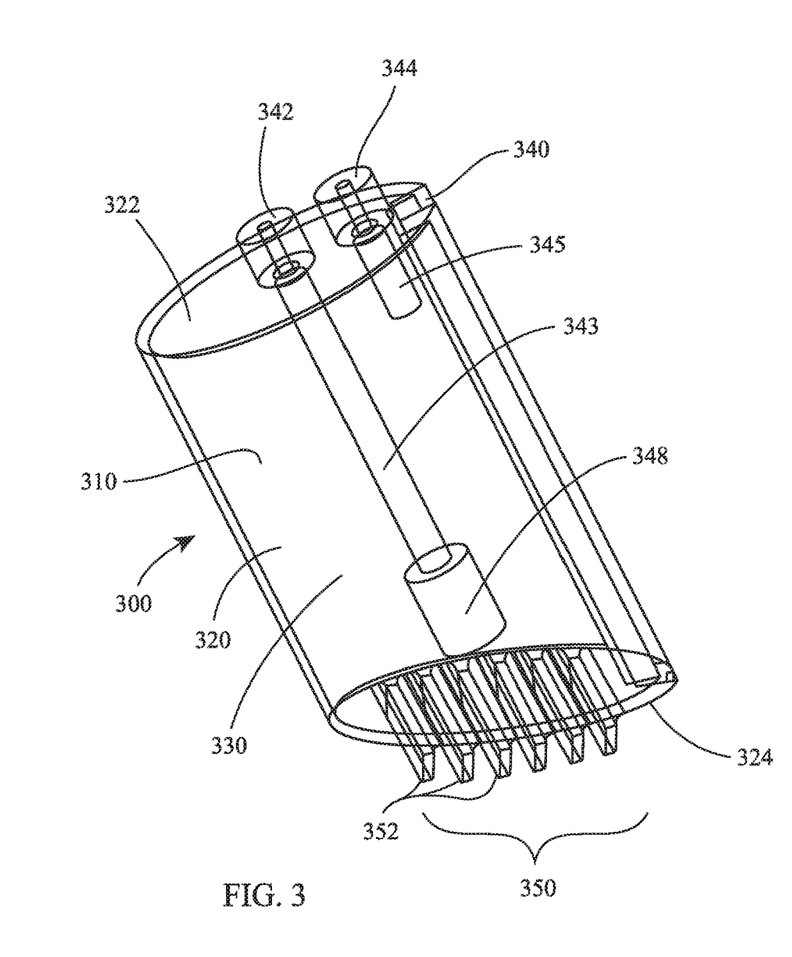
FIG. 3 is a perspective view of a fluid reservoir provided in accordance with the present disclosure and configured for use with the ultrasonic surgical instrument of FIG. 1.
Figure 4:
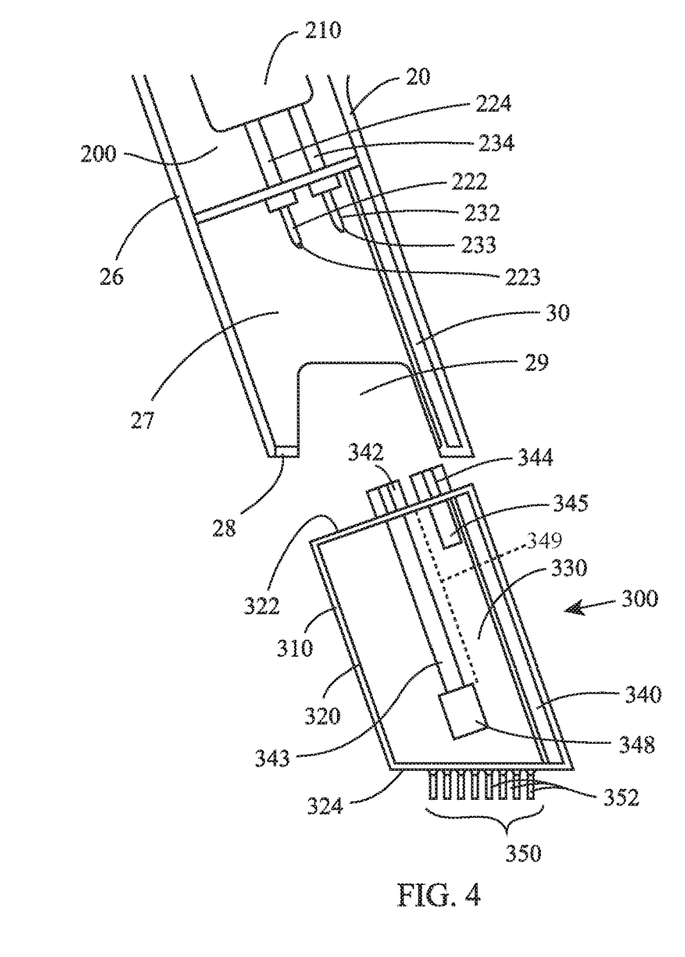
FIG. 4 is a side view of a fixed handle portion of the ultrasonic surgical instrument of FIG. 1 and the fluid reservoir of FIG. 3 disengaged therefrom.

With additional reference to FIGS. 3 and 4, fluid reservoir 300 includes a housing 310 defining a generally tubular body 320 having an insertion end 322 and a trailing end 324 enclosing therein a fluid chamber 330. Fluid reservoir 300 is pre-filled and stores therein a fluid, e.g., water, saline, etc. A guide slot 340 is defined within and extends along a substantial portion of the length of tubular body 320, e.g., at least 50% of the length of tubular body 320 or, in embodiments, at least 75% of the length of tubular body 320.

Insertion end 322 of fluid reservoir 300 includes a sealed inflow port 342 and a sealed outflow port 344. Inflow and outflow shafts 343, 345 extend from sealed inflow and outflow ports 342, 344, respectively, into fluid chamber 330. More specifically, inflow shaft 343 defines a relatively greater length and thus extends further through fluid chamber 330 such that the open end of inflow shaft 343 is positioned towards trailing end 324 of fluid reservoir 300, whereas outflow shaft 345 defines a relatively smaller length and thus does not extend as far through fluid chamber 330 but, rather, the open end of outflow shaft 345 is positioned towards insertion end 322 of fluid reservoir 300. By separating the open ends of inflow and outflow shafts 343, 345 at opposing ends of fluid chamber 330, the hotter, returned fluid from outflow shaft 345 is inhibited from being immediately drawn back out of fluid reservoir 300 though inflow shaft 343. As an alternative or in addition to using different length inflow and outflow shafts 343, 345, a dividing wall 349 (FIG. 4) may extend between inflow and outflow shafts 343, 345 to inhibit the hotter, returned fluid from outflow shaft 345 from being immediately drawn back out of fluid reservoir 300 though inflow shaft 343. Inflow shaft 343 may further include a filter 348 disposed at the open end thereof for filtering any fluid drawn into inflow shaft 343.

Trailing end 324 of fluid reservoir 300 includes a passive heat exchanger 350 disposed thereon. Passive heat exchanger 350 may include, for example, a plurality of spaced-apart fins 352 extending outwardly from trailing end 324. Fins 352 are configured to increase surface area and, thus, heat exchange between the interior and exterior of fluid reservoir 300 adjacent trailing end 324 of fluid reservoir 300. Further, with the open end of inflow shaft 343 positioned towards trailing end 324 of fluid reservoir 300, passive heat exchanger 350 helps cool fluid being drawn into inflow shaft 343.

Referring to FIGS. 1-4, in order to engage fluid reservoir 300 within ultrasonic surgical instrument 10, fluid reservoir 300, lead by insertion end 322 thereof is inserted into open lower end 28 of fixed handle portion 26 of housing 20 such that guide rail 30 is aligned with guide slot 340. As fluid reservoir 300 is advanced further into interior cavity 27 of fixed handle portion 26, guide rail 30 is received within guide slot 340 to guide insertion of fluid reservoir 300. Upon full insertion of fluid reservoir 300 into interior cavity 27 of fixed handle portion 26 of housing 20, sharp tips 223, 233 of hollow needles 222, 232 of inflow and outflow assemblies 220, 20 respectively, puncture and penetrate sealed inflow and outflow ports 342, 344, respectively, such that hollow needles 222, 232 are disposed in fluid communication with inflow and outflow shafts 343, 345, respectively. Fluid reservoir 300 may be maintained in engagement within fixed handle portion 26 via friction-fitting and/or other suitable releasable mechanical locking engagement.

In the fully inserted position of fluid reservoir 300, passive heat exchanger 350 remains external of fixed handle portion 26, extending therefrom so as to facilitate heat exchange. Further, opposing portions of body 320 of fluid reservoir 300 towards trailing end 324 thereof are exposed through cut-outs 29 of fixed handle portion 26 to enable grasping, disengagement, and withdrawal of fluid reservoir 300 from fixed handle portion 26.

Continuing with reference to FIGS. 1-4, ultrasonic surgical instrument 10 may be utilized to treat tissue clamped between blade 124 and clamp arm 102 or positioned adjacent blade 124. During such use, blade 124 may reach temperatures greater than 200° C. Thus, in order to facilitate cooling of blade 124 after use and/or in between usages, pump 210 of fluid management system 200 is activated, e.g., manually via an activation button (not shown) on housing 20 or remote therefrom or automatically after de-activation of ultrasonic transducer 80, to draw fluid from fluid reservoir 300 into inflow shaft 343, hollow needle 222, first conduit segment 224, and through second conduit segment 226, which extends into internal lumen 128 within blade 124 of waveguide 120. The fluid then returns proximally within the annular space defined between second conduit segment 226 and the interior wall of waveguide 120, into second conduit segment 236 of outflow fluid assembly 230, first conduit segment 234, needle 232, and outflow shaft 345, ultimately returning to fluid reservoir 300. Heat exchange 350 and the distance between the open ends of inflow and outflow shafts 343, 345, respectively, help ensure that the returned fluid is sufficiently cooled down before again being drawn into inflow shaft 343.

In order to remove fluid reservoir 300 after use, the opposing portions of body 320 of fluid reservoir 300 that are exposed through cut-outs 29 of fixed handle portion 26 are grasped and pulled away from housing 20 to thereby disengage and withdraw fluid reservoir 300 from fixed handle portion 26. Fluid reservoir 300 may be replaced with a new fluid reservoir 300 and may ultimately be discarded or reprocessed for subsequent use.

Figure 5:
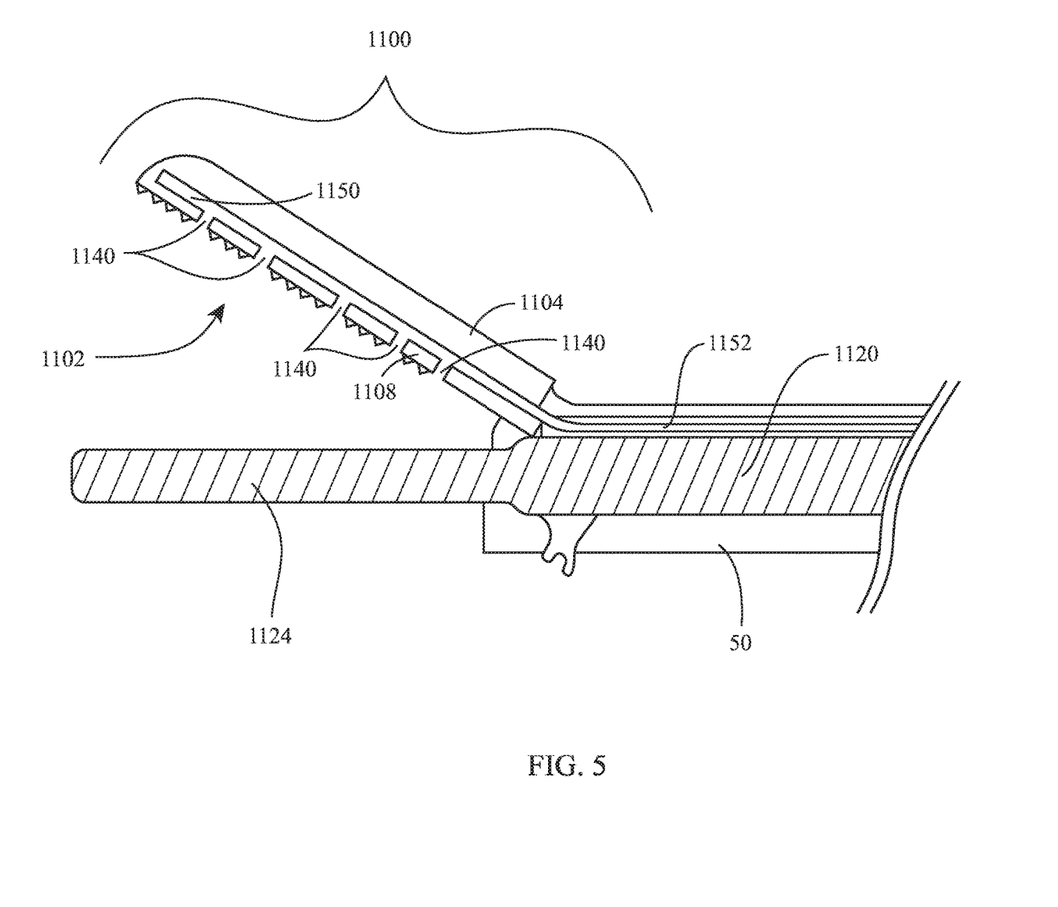
FIG. 5 is a longitudinal, cross-sectional view of the distal end of another ultrasonic surgical instrument provided in accordance with the present disclosure.

Turning now to FIG. 5, instead of a closed fluid circulation system such as detailed above, an open system may be provided wherein fluid is drawn from fluid reservoir 300 and is output at end effector assembly 1100. End effector assembly 1100 is similar to and may include any of the features of end effector assembly 100 (FIG. 1), except as specifically contradicted below.

End effector assembly 1100 is configured for use with ultrasonic surgical instrument 10 (FIG. 1) and includes a clamp arm 1102 and blade 1124 of waveguide 1120. Clamp arm 1102 is pivotable relative to blade 1124 between an open position and a clamping position for clamping tissue therebetween. Clamp arm 1102 includes a frame 1104 and a tissue pad 1108 engaged with frame 1104. Frame 1104 and/or tissue pad 1108 define a plurality of nozzles 1140 spaced-apart along a substantial portion, e.g., at least 50% or in embodiments at least 75%, of the length thereof and extending therethrough in communication with a longitudinally-extending lumen 1150 defined through frame 1104 and/or tissue pad 1108. Longitudinally-extending lumen 1150, in turn, is coupled to an inflow conduit 1152 that extends from clamp arm 1102 proximally through shaft 50 and into housing 20 of ultrasonic surgical instrument 10 (see FIGS. 1 and 2). Inflow conduit 1152 functions as the second conduit segment 226 of the inflow fluid assembly 220 (FIG. 2) and is configured to couple to fluid reservoir 300 similarly as detailed above with respect to inflow fluid assembly 220 (FIG. 2). However, as end effector assembly 1100 provides an open-loop configuration, no outflow fluid assembly or outflow port in fluid reservoir 300 need be provided (although such could be provided for use with both closed-loop and open-loop configurations, wherein the outflow portions are simply not used when an open-loop configuration is provided). Rather, in use, fluid is drawn from fluid reservoir 300 (FIG. 2) into inflow conduit 1152 and is pumped distally through inflow conduit 1152, ultimately spraying out from nozzles 1140 to cool blade 1124 along a substantial portion of the length of blade 1124.

While several embodiments of the disclosure have been shown in the drawings and described hereinabove, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic surgical instrument, comprising:
a housing defining a barrel portion and a fixed handle portion extending from the barrel portion, the fixed handle portion defining an open lower end and an internal cavity accessible from the open lower end, wherein the barrel portion comprises a proximal end, a distal end, and an intermediate portion defining a longitudinal axis, and wherein the fixed handle portion extends away from the intermediate portion at an angle transverse to the longitudinal axis of the barrel portion;
an ultrasonic transducer received at least partially within the barrel portion of the housing;
a waveguide defining a longitudinal axis and an internal lumen, operably coupled to the ultrasonic transducer, and extending distally from the housing to a blade configured to treat tissue with ultrasonic energy produced by the ultrasonic transducer and transmitted along the waveguide, wherein the waveguide is arranged substantially coaxial with the barrel portion;
a fluid management system disposed within the housing; and
a fluid reservoir insertable through the open lower end of the fixed handle portion to be releasably engageable within the internal cavity of the fixed handle portion of the housing, the fluid reservoir including a body, a leading end, and a trailing end enclosing a fluid chamber configured for storing fluid therein, the fluid reservoir further including inflow and outflow ports disposed at the leading end and a heat exchanger disposed at the trailing end,
wherein, upon engagement of the fluid reservoir within the internal cavity, the inflow and outflow ports are operably coupled with the fluid management system to enable fluid from the fluid reservoir to be delivered distally through the internal lumen and returned proximally from the internal lumen.

2. The ultrasonic surgical instrument according to claim 1, wherein the inflow and outflow ports of the fluid reservoir are sealed and wherein the fluid management system includes inflow and outflow needles configured to puncture the sealed inflow and outflow ports, respectively, to fluidly couple the fluid management system with the fluid reservoir.

3. The ultrasonic surgical instrument according to claim 1, wherein the fluid reservoir further includes inflow and outflow shafts operably coupled to the inflow and outflow ports, respectively, and extending into the fluid chamber.

4. The ultrasonic surgical instrument according to claim 3, wherein the inflow and outflow shafts define different lengths such that open ends of the inflow and outflow shafts are spaced-apart from one another along a length of the fluid chamber.

5. The ultrasonic surgical instrument according to claim 1, wherein the heat exchanger includes a plurality of fins configured to facilitate heat exchange between an exterior and an interior of the fluid reservoir.

6. The ultrasonic surgical instrument according to claim 5, wherein the heat exchange remains external of the housing when the fluid reservoir is engaged within the internal cavity.

7. The ultrasonic surgical instrument according to claim 1, wherein the fixed handle portion includes a guide rail disposed within the internal cavity and wherein the body of the fluid reservoir defines a guide slot configured to receive the guide rail to guide insertion of the fluid reservoir into the internal cavity.

8. The ultrasonic surgical instrument according to claim 1, wherein the fluid management system includes an inflow conduit communicating with the internal lumen defined by the waveguide for circulating fluid from the fluid reservoir through the waveguide.

9. The ultrasonic surgical instrument according to claim 1, wherein the fluid management system includes a fluid pump configured to pump fluid at least one of to or from the fluid reservoir.

10. The ultrasonic surgical instrument according to claim 1, wherein the internal lumen ends at a closed distal end of the waveguide.

11. The ultrasonic surgical instrument according to claim 1, further comprising an inflow shaft operably coupled to the inflow port and a filter operably coupled to the inflow shaft.

12. The ultrasonic surgical instrument according to claim 1, wherein the inflow port is operably coupled to an inflow conduit extending distally through the internal lumen of the waveguide for delivery of fluid from the fluid reservoir to the internal lumen of the waveguide.

13. The ultrasonic surgical instrument according to claim 12, wherein the inflow conduit extends distally through the internal lumen of the waveguide to a position adjacent but spaced from a closed distal end of the waveguide.

14. The ultrasonic surgical instrument according to claim 13, wherein the outflow port is operably coupled to an outflow conduit extending distally through the internal lumen of the waveguide for return of fluid from the internal lumen of the waveguide to the fluid reservoir.

15. The ultrasonic surgical instrument according to claim 1, wherein the fixed handle portion defines at least one cut-out for accessing the fluid reservoir when the fluid reservoir is inserted into the internal cavity of the fixed handle portion.

16. An ultrasonic surgical instrument, comprising:
a housing defining a barrel portion and a fixed handle portion extending from the barrel portion, the fixed handle portion defining an internal cavity and at least one cut-out portion, wherein the barrel portion comprises a proximal end, a distal end, and an intermediate portion defining a longitudinal axis, and wherein the fixed handle portion extends away from the intermediate portion at an angle transverse to the longitudinal axis of the barrel portion;
an ultrasonic transducer received at least partially within the barrel portion of the housing;
a waveguide defining a longitudinal axis and an internal lumen, operably coupled to the ultrasonic transducer, and extending distally from the housing to a blade configured to treat tissue with ultrasonic energy produced by the ultrasonic transducer and transmitted along the waveguide, wherein the waveguide is arranged substantially coaxial with the barrel portion;
a fluid management system disposed within the housing, the fluid management system including an inflow needle and an outflow needle; and
a fluid reservoir releasably engageable within the internal cavity of an open lower end of the fixed handle portion of the housing with at least a portion of the fluid reservoir exposed through the cut-out portion of the fixed handle portion, the fluid reservoir including a body, a leading end, and a trailing end enclosing a fluid chamber configured for storing fluid therein, the fluid reservoir further including inflow and outflow ports disposed at the leading end and a heat exchanger disposed at the trailing end,
wherein, upon engagement of the fluid reservoir within the internal cavity, the inflow port operably couples to the inflow needle and the outflow port operably couples to the outflow needle to enable fluid from the fluid reservoir to be delivered distally through the internal lumen and returned proximally from the internal lumen.

17. The ultrasonic surgical instrument according to claim 16, wherein the inflow and outflow ports of the fluid reservoir are sealed and wherein the inflow and outflow needles are configured to puncture the sealed inflow and outflow ports, respectively, when the fluid reservoir is engaged within the internal cavity of the fixed handle portion.

18. The ultrasonic surgical instrument according to claim 16, wherein the inflow needle and the outflow needle of the fluid management system are equal in length.

19. The ultrasonic surgical instrument according to claim 18, wherein the fluid reservoir further includes inflow and outflow shafts operably coupled to the inflow and outflow ports, respectively, and extending into the fluid chamber.

20. The ultrasonic surgical instrument according to claim 19, wherein the inflow and outflow shafts define different lengths such that open ends of the inflow and outflow shafts are spaced-apart from one another along a length of the fluid chamber.

* * * * *